United States Patent [19]
Omar et al.

[11] Patent Number: 5,912,328
[45] Date of Patent: Jun. 15, 1999

[54] METHOD FOR THE REMOVAL OF VIRUSES FROM PROTEIN SOLUTIONS

[75] Inventors: Adames Omar, Bern; Jean-Jacques Morgenthaler, Boll, both of Switzerland

[73] Assignee: Rotkreuzstiftung Zentrallaboratorium Blutspendedienst, Berne, Switzerland

[21] Appl. No.: 08/946,024

[22] Filed: Oct. 7, 1997

Related U.S. Application Data

[62] Division of application No. 08/426,054, Apr. 21, 1995, Pat. No. 5,696,236.

[51] Int. Cl.⁶ ........................................ A23G 1/00
[52] U.S. Cl. ..................... 530/412; 530/418; 530/364; 530/380; 530/383; 435/239
[58] Field of Search ................... 530/364, 380, 530/383, 412, 418; 435/239

[56] References Cited

U.S. PATENT DOCUMENTS

| | | | |
|---|---|---|---|
| 4,156,681 | 5/1979 | Schneider et al. | 260/122 |
| 4,305,870 | 12/1981 | Liu et al. | 260/112 B |
| 5,051,189 | 9/1991 | Farrah | 210/679 |
| 5,658,779 | 8/1997 | Krupey et al. | 435/239 |

FOREIGN PATENT DOCUMENTS

| | | |
|---|---|---|
| 085 917 A2 | 8/1983 | European Pat. Off. . |
| 02167232 | 6/1990 | Japan . |
| WO 84/00569 | 2/1984 | WIPO . |
| WO 91/10507 | 7/1991 | WIPO . |

OTHER PUBLICATIONS

Dahling and Wright, "A comparison of recovery of virus from wastewaters by beef extract–Celite, ferric chloride, and filter concentration procedures, " *Journal of Virological Methods* 22: 337–346, 1988.

Elödi et al., "Double Virus Inactivated F VIII Concentrate: Virus Validation and Clinical Efficacy of Haemoctin® (Biotest F VIII SDH), " *Animals of Hematology*, Supplement I70: 137, 1995.

Farrah et al., "Use of Modified Diatomaceous Earth for Removal and Recovery of Viruses in Water," *Applied and Environmental Microbiology* 57(9): 2502–2506, 1991.

Labedan, B., "In Vitro Study of the Phage T5 DNA Injection Process: Use of Columns of *Escherichia coli* Membranes Immobilized on Kieselguhr," *Virology* 85: 487–493, 1978.

Morgenthaler, J.–J., (eds)., *Current Studies in Hematology and Blood Transfusion No. 56: Virus Inactivation in Plasma Products*, Karger, New York, 1989.

Piszkiewicz et al., "Inactivation and Removal of Human Immunodeficiency Virus in Monoclonal Purified Antihemophilic Factor (Human) (Hemofil®M)," *Thrombosis Research* 55: 627–634, 1989.

Preston and Farrah, "Activation Thermodynamics of Virus Adsorption to Solids," *Applied and Enviromental Microbiology* 54(11): 2650–2654, 1988.

Wells et al., "Inactivation and partition of human T–cell lymphotropic virus, type III, during ethanol fractionation of plasma," *Transfusion* 26(2): 210–213, 1986.

Satlar et al., *Water Res.*, 13(7), 637–43, 1979.

Lawrence, A., *Symp. Ser. Immunobiol. Stand.*, 7, 217–26, 1967.

Globa et al., *Dopov. Akad. Nauk Ukr. RSR*, Ser. B, 3(11), 1036–8, 1971.

Stephan et al., *Z. Klin. Chem. Klin. Biochem.*, 6(3), 191–2, 1968.

*Primary Examiner*—Cecilia J. Tsang
*Assistant Examiner*—C. Delacroix-Muirheid
*Attorney, Agent, or Firm*—Seed and Berry LLP

[57] ABSTRACT

In order to separate viruses from protein solutions, particles of a solid phase are suspended in said protein solution. The solid phase is an adsorbent chosen from the group kieselguhr, silicic acid, clay minerals, metal hydroxide or oxihydrate, cellulose, perlite, and water insoluble synthetic polymers. Subsequently the solid phase together with the viruses that have adsorbed to it is separated from the fluid phase. The protein solution is brought into contact at least once with the solid phase for at least 10 minutes during which time a suspension is formed; subsequently the solid phase is separated from the liquid phase.

16 Claims, No Drawings

METHOD FOR THE REMOVAL OF VIRUSES FROM PROTEIN SOLUTIONS

CROSS REFERENCE TO RELATED APPLICATIONS

This application is a divisional of U.S. patent application Ser. No. 08/426,054, filed Apr. 21, 1995, now U.S. Pat. No. 5,696,236 which claims priority from European Patent Application No. 94810231.4, filed Apr. 25, 1994.

The present invention concerns a method for the removal of viruses from protein solutions, particularly from blood products that will be used for therapeutic and other medical purposes. The protein solution is brought into contact with an adsorbent to which the viruses will be bound.

In world war II a method was developed in the USA for the isolation of proteins from human blood plasma. These isolated proteins are then used medically as therapeutic agents. Albumin, immunoglobulins, fibrinogen, coagulation factors and numerous other proteins are examples of products of this method. Albumin is used, e.g., for burn patients or more generally in diseases in which the blood volume has to be increased. Immunoglobulins may be used in patients who are not able to synthesize protective antibodies themselves. Coagulation factor concentrates (in particular factor VIII and factor IX) are being used for hemophilia patients. In many cases these preparations are life-saving and therefore they have no substitute.

The methods for the separation of blood plasma in individual proteins are based on several different principles. The older methods which are still being used on a large scale are based on fractional precipitation of the proteins with ethanol and subsequent separation of the phases by centrifugation or filtration. In newer fractionation schemes, other separation methods are used as well, e.g., ion exchange chromatography or (immune) affinity chromatography. An integrated separation scheme usually comprises several different methods which are combined in an optimized process.

In the first years of use of plasma proteins in humans it became clear that products made from human blood also have disadvantages: they may transmit some infectious diseases which are caused by viruses. The most important virus in the beginning was viral hepatitis (hepatitis B). Later on other forms of Hepatitis became known (non-A non-B Hepatitis which was recently identified and named Hepatitis C). The best known virus which is transmitted by blood and blood products is the HIV, the causative agent of AIDS (acquired Immune Deficiency Syndrome). Apart from those mentioned so far there are some other viruses that may also be transmitted by plasma and plasma derivatives.

The safety of blood and blood derivatives may be increased by measures taken on different levels: (1) the collecting agencies try to exclude donors who are known to pose a high risk for transmitting infectious diseases. This is done with the aid of a questionnaire which allows to exclude people with increased risk factors. Persons with increased risk factors are e.g. those who suffer from certain diseases, those who visited certain countries shortly before donation, those who incur risks through their sexual activity or drug addicts who use contaminated needles. (2) Laboratory analyses allow the determination of infectious donations which can then be removed from further processing. Those two measures taken together result in removal of most infectious donations but not all: (a) the sensitivity of the test methods may be insufficient; (b) a test for a particular virus may not yet be available; for practical and economic reasons it is not possible to screen for all potential viruses; (c) the test does not detect the virus itself but rather the antibodies that are elicited in the infected person as a response to the virus infection. From the time of infection until detectable antibodies appear, usually a few days or weeks elapse (so called window). Antibody tests are useless during this period; (d) An infected donation may be released because of a clerical error. (3) For all these reasons, it is important that the safety with respect to transmission of viruses is assured during the production of blood and blood components. This is done with special steps that are introduced into the production process.

Such steps are developed now for blood products that contain cells (erythrocytes and platelet concentrates); they are, however, not yet in use. Plasma proteins on the other hand have been treated for several years now by special methods which allow either to inactivate or to eliminate viruses. One of the oldest methods is pasteurization (heating of the solution for 10 or more hours at a temperature of at least 60° C). This method has originally been developed for the inactivation of Hepatitis B viruses in Albumin solutions. Nowadays some manufacturers pasteurize, in addition to albumin, coagulation factor concentrates, immunoglobulins, and other plasma proteins in order to make them virus-safe.

A number of additional methods have been proposed in the last years in order to increase the safety of plasma proteins with respect to virus transmission. These methods are, among others: heating of the lyophilized end-product at 60 to 80° C. for 24 to 72 hours; treatment of the protein solution with β-propiolactone and ultraviolet light (introduces β-hydroxypropionic acid residues into protein); treatment with a combination of a solvent and a detergent (so called S/D treatment; destroys the lipid envelope of viruses); light treatment of the protein solution after addition of a suitable dye (photo dynamic virus inactivation; engenders modification of the nucleic acids). The methods for inactivation of viruses in plasma protein preparations have been reviewed in several articles [e.g., "Virus inactivation in plasma products"; Current Studies In Haematology and Blood Transfusion; J. J. Morgenthaler, edt.; Karger, Basel, 1989]. It is generally known that all these methods are much more efficient for enveloped than for small non-enveloped viruses.

Beside these methods that specifically aim at inactivating viruses, certain process steps often also improve virus safety of a product: during plasma fractionation, there is partitioning of the viruses and the proteins into the different compartments, e.g., a supernatant and a precipitate. This can result in a physical removal of viruses from a particular protein. It was shown e.g. that HIV is very efficiently partitioned away from immunoglobulins during ethanol fractionation [M. A. Wells and collaborators, Transfusion 26, 210–213 1986]. Other separation methods, e.g., immuno-affinity chromatography, may also result in viral removal from the end product [Piszkiewicz and collaborators, Thrombosis Research 55, 627–634, 1989].

In this context, the patents WO 00569/84 and EP-A-0 085 917 of Kenneth C. Hou have to be mentioned; they describe the preparation of a self-supporting fibrous matrix which contains at least 5% of silicium oxide or aluminium oxide particles in the μm size range. Such matrices or filters may be used to remove lipids or lipid-containing particles as well as hepatitis B surface antigen (HBsAg), which is bound to lipids or lipid-containing particles from fluids, in particular from biological fluids, e.g., from serum. The physical set-up of a self-supporting matrix is, however, completely different from the presently described removal of viruses by the addition of a powder.

Another patent which is relevant for the present invention describes the use of covalently modified carrier materials for the removal of viruses [H. Schwinn, WO 10507/91]. The materials are di-alkoxy phosphoric acid derivatives of the general formula:

$$\text{carrier-spacer-}O\text{-}PO(Oalk)_2$$

The spacer consists of an unbranched alkyl chain with 3 to 8 carbon atoms; alk is an alkyl group with 1 to 10 carbon atoms. In this case, the nature of the method is chromatography, not filtration.

The use of bentonite has been described in the preparation of intravenously applicable plasma derivatives for removing exogenous, deleterious activities, e.g., pre-kallikrein activator activity, activated coagulation factors, and esterase activity. The elimination of viruses is not mentioned in this document [D. T. H. Liu, A. L. S. Weidenbach, R. Pai, US-A-4 305 870].

The use of aluminium hydroxide for removing viruses from a coagulation factor concentrate has been mentioned in a meeting [S. Elödi and collaborators, Annals of Hematology, Supplement I, vol. 70, p. A35, 1995].

Companies that treat human blood still have the need for industrially applicable methods that allow a safe removal of viruses from protein solutions. In order to minimize the risk of infections for the patients who are treated with such products it is therefore the aim of the present invention to describe a method which allows the separation of viruses from protein solutions on an industrial scale; this method may be part of any current plasma fractionation scheme.

It was found that many viruses (either enveloped or non-enveloped) which may be present in protein solutions adsorb on certain materials e.g. modified cellulose, diatomacious earth, bentonites, volcanic earth, particles of artificial polymers etc. If the protein solutions are brought in contact with these materials for a sufficiently long time, the separation of a solution into a precipitate and a supernatant therefore results in further removal of viruses in addition to the removal effected by the precipitation step per se. This effect has been demonstrated for enveloped and non-enveloped viruses alike. The materials mentioned above have been introduced earlier into plasma fractionation as so-called filter aids in order to facilitate the separation of the precipitate and the supernatant during ethanol fractionation. The filter aids form a layer on top of the porous filter membranes and they promote filtration because they are permeable for liquid but not for solid particles. The filter aids prevent the clogging of the filter pores by small proteinaceous particles.

According to the present invention, viruses are removed from a protein solution by adsorption on a solid phase, said solid face being either suspended in solution in order to adsorb the viruses or having already been formed beforehand on a porous filter. The protein solution has to be brought into contact at least once with an adsorbent chosen from the group kieselguhr, diatomacious earths, silicic acid, clay minerals, metal hydroxide or -oxihydrate, cellulose, Perlite, and water insoluble synthetic polymers, or a mixture or combination of these materials; contact time is at least 10 min. Subsequently, the suspension is separated into supernatant and precipitate by filtration or any other suitable method.

Solid phases for this technology are, e.g., the filter aids Celite (Johns-Manville Corp.) Aerosil® (Degussa), perlite, heat expanded perlite, bentonite, or in general finely distributed solids which can be removed by filtration or centrifugation from a suspension. Substances like metal hydroxide gels (e.g. Alhydrogel $Al(OH)_3$ as a gel in water) are also suitable as will be shown in one of the examples.

The adsorption of viruses on the materials mentioned depends on the material used, the virus, and the environment. By systematic change of the environment, the "stickiness" of a particular virus onto the same material may be changed. It is, e.g., possible to markedly increase the adsorption of Semliki Forest virus, Sindbis virus, vesicular stomatitis virus or coxsackie virus on Celite 577 by lowering the pH-value of the medium. Other solution parameters like ionic strength, salts, and organic solvents also influence the adsorption of viruses and may be used in order to improve adsorption and therefore the removal of viruses from the protein solution. The preferred temperature for the method is 2° C. It is possible, however, to work at other temperatures, e.g. room temperature, provided the product is stable under those conditions.

Even a short treatment of the protein solution for only 10 minutes can result in a substantial removal of virus. It may, however, be advantageous to treat for a longer time in order to improve viral removal. Treatment times may be approximately 15 min, 30 min, ca. 1 h, ca. 2 h, ca. 6 h, ca. 8 h, ca. 12 h, ca. 14 h, ca. 16 h, ca. 20 h.

The removal of the adsorbent including the adsorbed viruses is done either by centrifugation or filtration. Centrifugation may be done in different ways, e.g., by a batch procedure or a continuous centrifugation. Centrifugal force and time of centrifugation have to be adjusted so that a clean separation of suspended material and supernatant is guaranteed. On a laboratory scale, filtration may be carried out with a Büchner funnel or a similar apparatus. On a larger scale (production) other equipment is preferred, e.g., filter presses or rotating filters.

EXAMPLE 1

One ml of virus suspension with known titer was added to 50 ml of immunoglobulin solution and mixed thoroughly. An aliquot was removed and the virus titer was assayed. Subsequently 0.1 g of Celite 577 was added and the suspension was mixed for 15 minutes at room temperature with a magnetic stirrer. The suspension was then filtered through a cellulose filter AF9. The viruses were assayed in the filtrate by titration (in all subsequent tables "E+X" is identical with "$10^X$"):

| Virus | Titer before filtration | Titer after filtration | | Geometric mean | Reduction factor |
|---|---|---|---|---|---|
| Semliki Forest virus (SFV) | 1.0E + 10 | 5.8E + 6 | 3.0E + 6 | 4.2E + 6 | 2.4E + 3 |
| Vesicular stomatitis virus (VSV) | 1.0E + 10 | 4.8E + 7 | 2.5E + 7 | 3.5E + 7 | 2.9E + 2 |

-continued

| Virus | Titer before filtration | Titer after filtration | | Geometric mean | Reduction factor |
|---|---|---|---|---|---|
| Bovine viral diarrhoea virus (BVDV) | 1.0E + 7 | 9.3E + 3 | 6.8E + 3 | 8.0E + 3 | 1.3E + 3 |
| Pseudorabies virus | 1.0E + 7 | 1.4E + 3 | 9.6E + 3 | 3.7E + 3 | 2.7E + 3 |
| Sindbis virus | 1.0E + 12 | 3.8E + 8 | 3.6E + 7 | 1.2E + 8 | 8.5E + 3 |
| Sindbis virus | 4.7E + 10 | 1.6E + 6 | 2.1E + 6 | 1.8E + 6 | 2.6E + 4 |
| Sindbis virus | 2.8E + 10 | 2.4E + 6 | 2.3E + 6 | 2.3E + 6 | 1.2E + 4 |
| Human immunodeficiency virus | 1.5E + 7 | 6.9E + 1 | 6.2E + 1 | 6.5E + 1 | 2.3E + 5 |
| Coxsackie virus | 1.0E + 7 | | <10 | <10 | >1.0E6 |
| Bovine parvovirus (BPV) | 1.0E + 7 | 3.2E + 3 | 4.8E + 3 | 3.9E + 3 | 2.6E + 3 |
| Bovine enterovirus | 3.00E + 07 | 9.80E + 02 | 5.00E + 03 | 2.2E + 3 | 1.4E + 4 |

The titers of all the viruses investigated were reduced by several orders of magnitude.

EXAMPLE 2

One ml of virus suspension of known titer was added to 50 ml each of immunoglobulin solution, pH 6.5, and mixed thoroughly. Subsequently, 4.5 g of alhydrogel suspension were added and the pH was adjusted with 0.1 N NaOH to 7.2. After 2 hours mixing on a magnetic stirrer at room temperature the pH was lowered with 0.2N HCl to 6. After another 12 hours of mixing 1 g of Celite 577 was added and mixing was continued for another 15 minutes. Finally the suspensions were filtered through a cellulose filter AF9 and the viruses were titrated in the filtrate.

| Virus | Titer before filtration | Titer after filtration | | Geometric mean | Reduction factor |
|---|---|---|---|---|---|
| SFV | 1.0E + 10 | 4.2E + 6 | 5.2E + 6 | 4.7E + 6 | 2.1E + 3 |
| Sindbis | 1.0E + 12 | 7.6E + 7 | 3.9E + 7 | 5.4E + 7 | 1.8E + 4 |
| VSV | 1.0E + 10 | <10 | <10 | <10 | >10E8 |
| Coxsackie | 1.0E + 7 | <10 | <10 | <10 | >10E6 |

It is obvious that the removal of VSV and Coxsackie virus is greatly improved by the addition of alhydrogel.

EXAMPLE 3

The so-called cryoprecipitate was removed from plasma by freezing and subsequent thawing at 2° C., followed by centrifugation. The supernatant after this treatment (so-called cryosupernatant) was used for further experiments. One ml of Hepatitis A virus (HAV) with a titer of $10^8$ TCID$_{50}$/ml was added to 85 ml of Cryosupernatant. Subsequently 0.43 g of Perlite J100 and 1.28 g of Celite 577 were added and the suspension was mixed for 15 minutes at room temperature. The suspension was filtered through a cellulose filter AF9 and the virus was titrated in the filtrate. Two independent determinations gave results of $6.3 \times 10^5$ and $2.5 \times 10^6$ TCID$_{50}$ total (geometric mean $1.2 \times 10^6$ TCID$_{50}$). This corresponds to a removal of HAV by a factor of 80.

EXAMPLE 4

One ml of an HAV preparation with a titer of $10^8$ TCID$_{50}$/ml was added to 85 ml of a solution of plasma proteins. After addition of 0.9 g of Perlite J100 and 0.9 g of Celite 577 the suspension was mixed for 10 minutes and subsequently filtered through a cellulose filter. Titration of HAV in the filtrate gave results of $1.0 \times 10^6$ and $1.9 \times 10^5$ TCID$_{50}$ total (geometric mean $4.4 \times 10^5$). The reduction factor was therefore 2.3 $10^2$.

EXAMPLE 5

One half of an ml of a HAV preparation (titer $10^8$ TCID$_{50}$/ml) was added to 35 ml of a fraction of human plasma proteins which contained the coagulation factor VIII in high concentration. After addition of 0.11 g of Bentonite and 30 min stirring, the suspension was filtered through a cellulose filter. The filtrate contained $7.9 \times 10^5$ and $6.3 \times 10^5$ TCID$_{50}$ total of HAV (geometric mean 7.0 $\times 10^5$) corresponding to a reduction factor of 70.

EXAMPLE 6

Four 50 ml aliquots each of immunoglobulin solution were adjusted to pH 7 and 5, respectively. To each solution, 1 ml of one of 4 virus suspensions and 0.1 g of Celite 577 was added. After 16 hours of stirring they were all filtered through a cellulose filter. The viruses were titrated in all filtrates.

| | Titer before filtration | Titer after filtration | | Geometric mean | Reduction factor |
|---|---|---|---|---|---|
| pH 7 Virus | | | | | |
| SFV | 1.0E + 10 | 7.5E + 6 | 8.9E + 6 | 8.2E + 6 | 1.2E + 3 |
| Sindbis | 1.0E + 12 | 4.2E + 8 | 1.9E + 8 | 2.8E + 8 | 3.5E + 3 |
| VSV | 1.0E + 10 | 2.0E + 7 | 4.8E + 7 | 3.1E + 7 | 3.2E + 2 |
| Coxsackie | 1.0E + 7 | | <10 | | >1.0E6 |
| pH 5 Virus | | | | | |
| SFV | 1.0E + 10 | 6.9E + 5 | 1.2E + 5 | 2.9E + 5 | 3.5E + 4 |
| Sindbis | 1.0E + 12 | 4.8E + 5 | 1.1E + 5 | 2.3E + 5 | 4.4E + 6 |
| VSV | 1.0E + 10 | 2.1E + 3 | 5.5E + 3 | 3.4E + 3 | 2.9E + 6 |
| Coxsackie | 1.0E + 7 | | <10 | | >1.0E6 |

In most cases, the reduction factor is higher at low pH than at high pH.

EXAMPLE 7

One ml of virus suspension was added to 50 ml each of immunoglobulin solution. 0.1 g of Celite 577 were added and the suspensions were filtered through a cellulose filter after 15 minutes of stirring. Viruses were assayed in the filtrate by titration. All experiments were done at 4° C. as well as at 20° C.

| Virus | Titer before filtration | 20° C. | | 4° C. | |
|---|---|---|---|---|---|
| | | Titer after filtration | Reduction factor | Titer after filtration | Reduction factor |
| SFV | 1.0E + 10 | 7.5E + 6 | 1.3E + 3 | 8.9E + 6 | 1.1E + 3 |
| Sindbis | 1.0E + 12 | 4.3E + 8 | 2.4E + 3 | 1.1E + 8 | 9.1E + 3 |
| VSV | 1.0E + 10 | 4.8E + 7 | 2.1E + 2 | 2.5E + 7 | 4.0E + 2 |

Considering the accuracy that can be expected from virus titration experiments, the reduction of virus titer by filtration does not depend on temperature, within the temperature limits investigated.

EXAMPLE 8

One ml of SFV suspension was added to 50 ml of immunoglobulin solution. Subsequently 0.1 g of Celite was added and the mixture was stirred for 15 minutes. The suspension was filtered through a cellulose filter. The SFV titer was assayed in the filtrate. Addition of Celite, stirring, filtration, and virus assay were repeated twice with the resulting filtrates.

| | Titer before filtration | Titer after filtration | Reduction factor |
|---|---|---|---|
| 1. Filtration | 1.0E + 10 | 1.2E + 7 | 8.3E + 2 |
| 2. Filtration | 1.2E + 7 | 9.4E + 5 | 1.3E + 1 |
| 3. Filtration | 9.4E + 5 | 1.2E + 4 | 7.8E + 1 |

This example shows that several filtrations in sequence remove additional virus from the same solution.

We claim:

1. A method for separating viruses from a protein solution comprising suspending particles of an adsorbent for the purpose of adsorption of viruses being present in the protein solution, and separating adsorbent with adsorbed viruses from the protein solution, wherein the protein solution is brought into contact with at least one adsorbent selected from the group consisting of clay minerals, metal oxihydrate, and cellulose for a time of at least 10 minutes during which a suspension is formed and after which time the adsorbent is separated from the protein solution.

2. The method according to claim 1, wherein the adsorbent is separated from the protein solution by centrifugation or filtration.

3. The method according to claim 1, wherein the protein solution is a preparation based on human blood plasma.

4. The method according to any of claims 1–3, wherein the adsorbent is an insoluble metal oxihydrate.

5. The method according to claim 1, wherein the adsorbent is cellulose.

6. The method according to claim 1, wherein the adsorbent is talcum.

7. The method according to claim 1, wherein the adsorbent is present in the form of a gel.

8. The method according to claim 1, wherein the protein solution is contacted at least twice with a fresh amount of the adsorbent.

9. The method according to claim 8, wherein the contact between the adsorbent and the protein solution is done at least 3 times, each time with a fresh supply of adsorbent.

10. The method according to claim 1, wherein the pH value of the protein solution is between 4 and 7.

11. The method according to claim 10, wherein the pH value and/or the ionic strength of the protein solution is changed at least once during the contact time of the adsorbent with the protein solution.

12. The method according to claim 11, wherein the pH value is lowered during the contact time of the adsorbent with the protein solution.

13. The method according to claim 1, wherein the contact time between the protein solution and the adsorbent is between 3 to 48 hours.

14. The method according to claim 1, wherein the contact time between the protein solution and the adsorbent is between 30 minutes and 12 hours.

15. The method of claim 1, wherein the temperature of the protein solution is between 9 and 20° C.

16. The method of claim 1, wherein the temperature of the protein solution is about 2° C.

* * * * *